US009730600B2

(12) United States Patent
Thakur et al.

(10) Patent No.: US 9,730,600 B2
(45) Date of Patent: Aug. 15, 2017

(54) MEDICAL DEVICE FOR HIGH RESOLUTION MAPPING USING LOCALIZED MATCHING

(71) Applicant: BOSTON SCIENTIFIC SCIMED, INC., Maple Grove, MN (US)

(72) Inventors: Pramodsingh Hirasingh Thakur, Woodbury, MN (US); Allan C. Shuros, St. Paul, MN (US); Barun Maskara, Blaine, MN (US); Shibaji Shome, Arden Hills, MN (US); Shantha Arcot-Krishnamurthy, Renton, WA (US); Sunipa Saha, Shoreview, MN (US); Scott A. Meyer, Lakeville, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 14/527,090

(22) Filed: Oct. 29, 2014

(65) Prior Publication Data

US 2015/0119672 A1     Apr. 30, 2015

Related U.S. Application Data

(60) Provisional application No. 61/898,312, filed on Oct. 31, 2013.

(51) Int. Cl.
*A61B 5/042* (2006.01)
*A61B 5/046* (2006.01)
(Continued)

(52) U.S. Cl.
CPC ............ *A61B 5/042* (2013.01); *A61B 5/046* (2013.01); *A61B 5/0422* (2013.01);
(Continued)

(58) Field of Classification Search
None
See application file for complete search history.

(56) References Cited

U.S. PATENT DOCUMENTS 4,754,753 A * 7/1988 King .................... A61N 1/3621
600/512
4,799,493 A * 1/1989 DuFault ............... A61N 1/3956
600/518
(Continued)

FOREIGN PATENT DOCUMENTS

CN         101313334 A     11/2008
CN         101317194 A     12/2008
(Continued)

OTHER PUBLICATIONS

Habel, Nicole et al., "The Temporal Variability of Dominant Frequency and Complex Fractionated Atrial Electrograms Constrains the Validity of Sequential Mapping in Human Atrial Fibrillation", Heart Rhythm, 7(5):586-593, May 1, 2010.
(Continued)

*Primary Examiner* — Kennedy Schaetzle
(74) *Attorney, Agent, or Firm* — Faegre Baker Daniels LLP (57) ABSTRACT

Medical devices and methods for using medical devices are disclosed. An example mapping medical device may include a catheter shaft with a plurality of electrodes. The catheter shaft may be coupled to a processor. The processor may be capable of collecting a first set of signals from a first location, collecting a second set of signals from a second location, characterizing the first set of signals over a first time period, characterizing the second set of signals over a second time period, comparing the first set of signals to the second set of signals and matching a first signal from the first set of signals with a second signal from the second set of signals.

20 Claims, 5 Drawing Sheets

(51) Int. Cl.
*A61B 5/0452* (2006.01)
*A61B 5/0464* (2006.01)
*A61B 5/00* (2006.01)
*A61B 18/14* (2006.01)
*A61B 18/00* (2006.01)

(52) U.S. Cl.
CPC .......... *A61B 5/0452* (2013.01); *A61B 5/0464* (2013.01); *A61B 5/7246* (2013.01); *A61B 18/1492* (2013.01); *A61B 2018/0016* (2013.01); *A61B 2018/00267* (2013.01); *A61B 2018/00357* (2013.01); *A61B 2018/00577* (2013.01); *A61B 2018/00839* (2013.01); *A61B 2018/1465* (2013.01); *A61B 2018/1467* (2013.01)

(56) References Cited

U.S. PATENT DOCUMENTS

| | | |
|---|---|---|
| 5,038,791 A * | 8/1991 | Collins ............. A61B 5/0402 600/509 |
| 5,158,092 A * | 10/1992 | Glace ............. A61B 5/0422 600/518 |
| 5,254,088 A | 10/1993 | Lundquist et al. |
| 5,292,348 A | 3/1994 | Saumarez et al. |
| 5,383,874 A | 1/1995 | Jackson et al. |
| 5,433,198 A * | 7/1995 | Desai ............. A61B 5/0422 600/374 |
| 5,485,849 A | 1/1996 | Panescu et al. |
| 5,487,391 A | 1/1996 | Panescu |
| 5,494,042 A | 2/1996 | Panescu et al. |
| 5,527,292 A | 6/1996 | Adams et al. |
| 5,546,940 A | 8/1996 | Panescu et al. |
| 5,577,509 A | 11/1996 | Panescu et al. |
| 5,582,609 A | 12/1996 | Swanson et al. |
| 5,595,183 A | 1/1997 | Swanson et al. |
| 5,598,848 A | 2/1997 | Swanson et al. |
| 5,601,088 A | 2/1997 | Swanson et al. |
| 5,605,157 A | 2/1997 | Panescu et al. |
| 5,609,157 A | 3/1997 | Panescu et al. |
| 5,630,425 A | 5/1997 | Panescu et al. |
| 5,647,870 A | 7/1997 | Kordis et al. |
| 5,657,755 A * | 8/1997 | Desai ............. A61B 5/0422 600/374 |
| 5,688,267 A | 11/1997 | Panescu et al. |
| 5,702,386 A | 12/1997 | Stern et al. |
| 5,711,305 A | 1/1998 | Swanson et al. |
| 5,722,402 A | 3/1998 | Swanson et al. |
| 5,722,403 A | 3/1998 | McGee et al. |
| 5,722,416 A | 3/1998 | Swanson et al. |
| 5,732,698 A | 3/1998 | Swanson et al. |
| 5,735,846 A | 4/1998 | Panescu et al. |
| 5,740,808 A | 4/1998 | Panescu et al. |
| 5,752,518 A | 5/1998 | McGee et al. |
| 5,755,715 A | 5/1998 | Stern et al. |
| 5,769,847 A | 6/1998 | Panescu et al. |
| 5,792,064 A | 8/1998 | Panescu et al. |
| 5,795,303 A | 8/1998 | Swanson et al. |
| 5,797,903 A | 8/1998 | Swanson et al. |
| 5,797,905 A | 8/1998 | Fleischman et al. |
| 5,810,740 A * | 9/1998 | Paisner ............. A61B 5/6852 600/515 |
| 5,810,802 A | 9/1998 | Panescu et al. |
| 5,830,213 A | 11/1998 | Panescu et al. |
| 5,833,621 A | 11/1998 | Panescu et al. |
| 5,836,874 A | 11/1998 | Swanson et al. |
| 5,840,076 A | 11/1998 | Swanson et al. |
| 5,846,238 A | 12/1998 | Jackson et al. |
| 5,846,239 A | 12/1998 | Swanson et al. |
| 5,848,969 A | 12/1998 | Panescu et al. |
| 5,853,409 A | 12/1998 | Swanson et al. |
| 5,853,411 A | 12/1998 | Whayne et al. |
| 5,868,680 A | 2/1999 | Steiner et al. |
| 5,868,736 A | 2/1999 | Swanson et al. |
| 5,871,483 A | 2/1999 | Jackson et al. |
| 5,876,336 A | 3/1999 | Swanson et al. |
| 5,879,348 A | 3/1999 | Owens et al. |
| 5,891,136 A | 4/1999 | McGee et al. |
| 5,904,651 A | 5/1999 | Swanson et al. |
| 5,904,680 A | 5/1999 | Kordis et al. |
| 5,906,614 A | 5/1999 | Stern et al. |
| 5,908,445 A | 6/1999 | Whayne et al. |
| 5,911,739 A | 6/1999 | Kordis et al. |
| 5,916,163 A | 6/1999 | Panescu et al. |
| 5,925,038 A | 7/1999 | Panescu et al. |
| 5,928,228 A | 7/1999 | Kordis et al. |
| 5,935,079 A | 8/1999 | Swanson et al. |
| 5,941,251 A | 8/1999 | Panescu et al. |
| 5,954,661 A | 9/1999 | Greenspon et al. |
| 5,954,662 A | 9/1999 | Swanson et al. |
| 5,961,513 A | 10/1999 | Swanson et al. |
| 5,968,040 A | 10/1999 | Swanson et al. |
| 6,014,581 A | 1/2000 | Whayne et al. |
| 6,014,590 A | 1/2000 | Whayne et al. |
| 6,016,442 A | 1/2000 | Hsu et al. |
| 6,022,346 A | 2/2000 | Panescu et al. |
| 6,030,379 A | 2/2000 | Panescu et al. |
| 6,030,382 A | 2/2000 | Fleischman et al. |
| 6,035,226 A | 3/2000 | Panescu et al. |
| 6,047,218 A | 4/2000 | Whayne et al. |
| 6,049,732 A | 4/2000 | Panescu et al. |
| 6,053,912 A | 4/2000 | Panescu et al. |
| 6,056,745 A | 5/2000 | Panescu et al. |
| 6,070,094 A | 5/2000 | Swanson et al. |
| 6,071,278 A | 6/2000 | Panescu et al. |
| 6,076,012 A | 6/2000 | Swanson et al. |
| 6,086,532 A | 7/2000 | Panescu et al. |
| 6,095,150 A | 8/2000 | Panescu et al. |
| 6,101,409 A | 8/2000 | Swanson et al. |
| 6,101,410 A | 8/2000 | Panescu et al. |
| 6,106,460 A | 8/2000 | Panescu et al. |
| 6,106,522 A | 8/2000 | Fleischman et al. |
| 6,113,591 A | 9/2000 | Whayne et al. |
| 6,115,626 A | 9/2000 | Whayne et al. |
| 6,123,702 A | 9/2000 | Swanson et al. |
| 6,129,669 A | 10/2000 | Panescu et al. |
| 6,129,724 A | 10/2000 | Fleischman et al. |
| 6,153,337 A | 11/2000 | Carlson et al. |
| 6,162,184 A | 12/2000 | Swanson et al. |
| 6,165,169 A | 12/2000 | Panescu et al. |
| 6,171,306 B1 | 1/2001 | Swanson et al. |
| 6,179,835 B1 | 1/2001 | Panescu et al. |
| 6,183,468 B1 | 2/2001 | Swanson et al. |
| 6,188,924 B1 | 2/2001 | Swanson et al. |
| 6,192,266 B1 | 2/2001 | Dupree et al. |
| 6,197,021 B1 | 3/2001 | Panescu et al. |
| 6,206,831 B1 | 3/2001 | Suorsa et al. |
| 6,216,043 B1 | 4/2001 | Swanson et al. |
| 6,221,013 B1 | 4/2001 | Panescu et al. |
| 6,233,491 B1 | 5/2001 | Kordis et al. |
| 6,245,061 B1 | 6/2001 | Panescu et al. |
| 6,245,065 B1 | 6/2001 | Panescu et al. |
| 6,256,540 B1 | 7/2001 | Panescu et al. |
| 6,289,239 B1 | 9/2001 | Panescu et al. |
| 6,293,943 B1 | 9/2001 | Panescu et al. |
| 6,330,473 B1 | 12/2001 | Swanson et al. |
| 6,353,751 B1 | 3/2002 | Swanson et al. |
| 6,370,435 B2 | 4/2002 | Panescu et al. |
| 6,389,311 B1 | 5/2002 | Whayne et al. |
| 6,391,024 B1 | 5/2002 | Sun et al. |
| 6,428,536 B2 | 8/2002 | Panescu et al. |
| 6,456,864 B1 | 9/2002 | Swanson et al. |
| 6,471,699 B1 | 10/2002 | Fleischman et al. |
| 6,487,441 B1 | 11/2002 | Swanson et al. |
| 6,488,679 B1 | 12/2002 | Swanson et al. |
| 6,490,468 B2 | 12/2002 | Panescu et al. |
| 6,494,880 B1 | 12/2002 | Swanson et al. |
| 6,500,172 B1 | 12/2002 | Panescu et al. |
| 6,508,765 B2 | 1/2003 | Suorsa et al. |
| 6,516,807 B1 | 2/2003 | Panescu et al. |
| 6,522,913 B2 | 2/2003 | Panescu et al. |
| 6,542,773 B2 | 4/2003 | Dupree et al. |
| 6,565,511 B2 | 5/2003 | Panescu et al. |

(56) References Cited

U.S. PATENT DOCUMENTS

| | | |
|---|---|---|
| 6,569,160 B1 | 5/2003 | Goldin et al. |
| 6,574,492 B1 | 6/2003 | Ben-Haim et al. |
| 6,597,955 B2 | 7/2003 | Panescu et al. |
| 6,600,948 B2 | 7/2003 | Ben-Haim et al. |
| 6,615,073 B1 | 9/2003 | Panescu et al. |
| 6,625,482 B1 | 9/2003 | Panescu et al. |
| 6,647,281 B2 | 11/2003 | Morency |
| 6,652,513 B2 | 11/2003 | Panescu et al. |
| 6,658,279 B2 | 12/2003 | Swanson et al. |
| 6,668,198 B2 | 12/2003 | Swanson et al. |
| 6,735,465 B2 | 5/2004 | Panescu |
| 6,736,811 B2 | 5/2004 | Panescu et al. |
| 6,746,401 B2 | 6/2004 | Panescu |
| 6,788,969 B2 | 9/2004 | Dupree et al. |
| 6,790,206 B2 | 9/2004 | Panescu |
| 6,824,515 B2 | 11/2004 | Suorsa et al. |
| 6,895,267 B2 | 5/2005 | Panescu et al. |
| 6,950,689 B1 | 9/2005 | Willis et al. |
| 6,978,168 B2 * | 12/2005 | Beatty ............... A61B 5/04085 600/513 |
| 7,123,954 B2 | 10/2006 | Narayan et al. |
| 7,194,294 B2 | 3/2007 | Panescu et al. |
| 7,364,546 B2 | 4/2008 | Panescu et al. |
| 7,505,810 B2 | 3/2009 | Harlev et al. |
| 7,515,954 B2 | 4/2009 | Harlev et al. |
| 7,565,208 B2 | 7/2009 | Harris et al. |
| 7,582,084 B2 | 9/2009 | Swanson et al. |
| 7,676,264 B1 | 3/2010 | Pillai et al. |
| 7,699,829 B2 | 4/2010 | Harris et al. |
| 7,729,752 B2 | 6/2010 | Harlev et al. |
| 7,794,404 B1 | 9/2010 | Gutfinger et al. |
| 7,841,986 B2 | 11/2010 | He et al. |
| 7,925,349 B1 | 4/2011 | Wong et al. |
| 7,930,018 B2 | 4/2011 | Harlev et al. |
| 7,937,136 B2 | 5/2011 | Harlev et al. |
| 7,945,326 B1 | 5/2011 | Wong et al. |
| 7,946,995 B1 | 5/2011 | Koh et al. |
| 7,953,475 B2 | 5/2011 | Harlev et al. |
| 7,957,791 B2 | 6/2011 | Harlev et al. |
| 7,957,792 B2 | 6/2011 | Harlev et al. |
| 7,957,813 B1 | 6/2011 | Persson et al. |
| 8,010,196 B1 | 8/2011 | Wong et al. |
| 8,019,419 B1 | 9/2011 | Panescu et al. |
| 8,032,218 B2 | 10/2011 | Wong et al. |
| 8,038,625 B2 | 10/2011 | Afonso et al. |
| 8,065,005 B1 | 11/2011 | Wong et al. |
| 8,103,327 B2 | 1/2012 | Harlev et al. |
| 8,103,338 B2 | 1/2012 | Harlev et al. |
| 8,128,617 B2 | 3/2012 | Bencini et al. |
| 8,137,343 B2 | 3/2012 | Harlev et al. |
| 8,167,876 B2 | 5/2012 | Harlev et al. |
| 8,175,680 B2 | 5/2012 | Panescu |
| 8,202,224 B2 | 6/2012 | Gutfinger et al. |
| 8,208,999 B2 | 6/2012 | Wenzel et al. |
| 8,280,511 B2 | 10/2012 | Zhao et al. |
| 8,306,623 B2 | 11/2012 | Wong et al. |
| 8,369,922 B2 | 2/2013 | Paul et al. |
| 8,386,049 B2 | 2/2013 | Persson et al. |
| 8,406,866 B2 | 3/2013 | Deno et al. |
| 8,414,579 B2 | 4/2013 | Kim et al. |
| 8,449,535 B2 | 5/2013 | Deno et al. |
| 8,504,152 B2 | 8/2013 | Wenzel et al. |
| 8,504,153 B2 | 8/2013 | Wenzel et al. |
| 8,554,333 B2 | 10/2013 | Wu et al. |
| 8,571,647 B2 | 10/2013 | Harlev et al. |
| 8,600,497 B1 | 12/2013 | Yang et al. |
| 8,712,519 B1 | 4/2014 | Panescu et al. |
| 9,144,391 B2 | 9/2015 | Thakur et al. |
| 9,332,920 B2 | 5/2016 | Thakur et al. |
| 2001/0000791 A1 | 5/2001 | Suorsa et al. |
| 2001/0009976 A1 | 7/2001 | Panescu et al. |
| 2001/0018608 A1 | 8/2001 | Panescu et al. |
| 2001/0020126 A1 | 9/2001 | Swanson et al. |
| 2001/0025175 A1 | 9/2001 | Panescu et al. |
| 2001/0044585 A1 | 11/2001 | Dupree et al. |
| 2002/0058870 A1 | 5/2002 | Panescu et al. |
| 2002/0065465 A1 | 5/2002 | Panescu et al. |
| 2002/0099415 A1 | 7/2002 | Panescu et al. |
| 2002/0111548 A1 | 8/2002 | Swanson et al. |
| 2002/0115941 A1 | 8/2002 | Whayne et al. |
| 2002/0143250 A1 | 10/2002 | Panescu et al. |
| 2002/0161422 A1 | 10/2002 | Swanson et al. |
| 2002/0193790 A1 | 12/2002 | Fleischman et al. |
| 2002/0198520 A1 | 12/2002 | Coen et al. |
| 2003/0028118 A1 | 2/2003 | Dupree et al. |
| 2003/0055419 A1 | 3/2003 | Panescu et al. |
| 2003/0065322 A1 | 4/2003 | Panescu et al. |
| 2003/0078494 A1 | 4/2003 | Panescu et al. |
| 2003/0078509 A1 | 4/2003 | Panescu |
| 2003/0088244 A1 | 5/2003 | Swanson et al. |
| 2003/0093067 A1 | 5/2003 | Panescu |
| 2003/0093069 A1 | 5/2003 | Panescu et al. |
| 2003/0144655 A1 | 7/2003 | Panescu |
| 2003/0153907 A1 | 8/2003 | Suorsa et al. |
| 2003/0158477 A1 | 8/2003 | Panescu |
| 2003/0199863 A1 | 10/2003 | Swanson et al. |
| 2003/0208123 A1 | 11/2003 | Panescu |
| 2004/0015065 A1 | 1/2004 | Panescu et al. |
| 2004/0097803 A1 | 5/2004 | Panescu |
| 2004/0254437 A1 | 12/2004 | Hauck et al. |
| 2005/0007091 A1 | 1/2005 | Makeig et al. |
| 2005/0177151 A1 | 8/2005 | Coen et al. |
| 2005/0197657 A1 | 9/2005 | Goth et al. |
| 2005/0215945 A1 | 9/2005 | Harris et al. |
| 2005/0245949 A1 | 11/2005 | Goth et al. |
| 2005/0261599 A1 | 11/2005 | Shvilkin et al. |
| 2006/0030833 A1 | 2/2006 | Harris et al. |
| 2006/0064083 A1 | 3/2006 | Khalaj et al. |
| 2006/0074336 A1 | 4/2006 | Grieve et al. |
| 2006/0089688 A1 | 4/2006 | Panescu |
| 2006/0116594 A1 | 6/2006 | Zhang et al. |
| 2006/0135957 A1 | 6/2006 | Panescu |
| 2006/0184166 A1 | 8/2006 | Valle et al. |
| 2007/0055227 A1 | 3/2007 | Khalaj et al. |
| 2007/0073179 A1 | 3/2007 | Afonso et al. |
| 2007/0073286 A1 | 3/2007 | Panescu et al. |
| 2007/0156048 A1 | 7/2007 | Panescu et al. |
| 2007/0299351 A1 | 12/2007 | Harlev et al. |
| 2007/0299352 A1 | 12/2007 | Harlev et al. |
| 2007/0299353 A1 | 12/2007 | Harlev et al. |
| 2008/0190438 A1 | 8/2008 | Harlev et al. |
| 2008/0222109 A1 | 9/2008 | Sakurai |
| 2008/0249424 A1 | 10/2008 | Harlev et al. |
| 2008/0262361 A1 | 10/2008 | Gutfinger et al. |
| 2009/0018597 A1 | 1/2009 | Wenzel et al. |
| 2009/0171274 A1 | 7/2009 | Harlev et al. |
| 2009/0171345 A1 | 7/2009 | Miller et al. |
| 2009/0177071 A1 | 7/2009 | Harlev et al. |
| 2009/0177072 A1 | 7/2009 | Harlev et al. |
| 2009/0253976 A1 | 10/2009 | Harlev et al. |
| 2009/0281439 A1 | 11/2009 | Harlev et al. |
| 2009/0287267 A1 | 11/2009 | Wenzel et al. |
| 2009/0299211 A1 | 12/2009 | Wenzel et al. |
| 2010/0004712 A1 | 1/2010 | Zhao et al. |
| 2010/0023085 A1 | 1/2010 | Wu et al. |
| 2010/0030294 A1 | 2/2010 | Wong et al. |
| 2010/0106009 A1 | 4/2010 | Harlev et al. |
| 2010/0106154 A1 | 4/2010 | Harlev et al. |
| 2010/0274150 A1 | 10/2010 | Harlev et al. |
| 2010/0286550 A1 | 11/2010 | Harlev et al. |
| 2010/0286551 A1 | 11/2010 | Harlev et al. |
| 2010/0298651 A1 | 11/2010 | Moon et al. |
| 2010/0305433 A1 | 12/2010 | Harlev et al. |
| 2010/0324414 A1 | 12/2010 | Harlev et al. |
| 2011/0028821 A1 | 2/2011 | Bojovic et al. |
| 2011/0105928 A1 | 5/2011 | Bojovic et al. |
| 2011/0112413 A1 | 5/2011 | Panescu et al. |
| 2011/0112414 A1 | 5/2011 | Panescu et al. |
| 2011/0112415 A1 | 5/2011 | Bojovic et al. |
| 2011/0160574 A1 | 6/2011 | Harlev et al. |
| 2011/0166472 A1 | 7/2011 | Björling et al. |
| 2011/0184300 A1 | 7/2011 | Shvilkin et al. |
| 2011/0190625 A1 | 8/2011 | Harlev et al. |
| 2011/0202113 A1 | 8/2011 | Persson et al. |

(56) References Cited

U.S. PATENT DOCUMENTS

| | | | |
|---|---|---|---|
| 2011/0251505 | A1 | 10/2011 | Narayan et al. |
| 2011/0275949 | A1 | 11/2011 | Harlev et al. |
| 2011/0282186 | A1 | 11/2011 | Harlev et al. |
| 2011/0282187 | A1 | 11/2011 | Harlev et al. |
| 2012/0053470 | A1 | 3/2012 | Wong et al. |
| 2012/0078077 | A1 | 3/2012 | Harlev et al. |
| 2012/0130267 | A1 | 5/2012 | Harlev et al. |
| 2012/0143030 | A1 | 6/2012 | Harlev et al. |
| 2012/0184858 | A1 | 7/2012 | Harlev et al. |
| 2012/0184863 | A1 | 7/2012 | Harlev et al. |
| 2012/0184864 | A1 | 7/2012 | Harlev et al. |
| 2012/0184865 | A1 | 7/2012 | Harlev et al. |
| 2012/0253161 | A1 | 10/2012 | Harlev et al. |
| 2012/0277574 | A1 | 11/2012 | Panescu |
| 2012/0296569 | A1 | 11/2012 | Shahaf et al. |
| 2013/0060245 | A1 | 3/2013 | Grunewald et al. |
| 2013/0096447 | A1 | 4/2013 | Dhawan et al. |
| 2013/0123775 | A1 | 5/2013 | Grunewald et al. |
| 2013/0137999 | A1 | 5/2013 | Wenzel et al. |
| 2013/0204124 | A1 | 8/2013 | Duindam et al. |
| 2013/0303892 | A1 | 11/2013 | Zhao et al. |
| 2013/0303945 | A1 | 11/2013 | Blumenkranz et al. |
| 2014/0336518 | A1* | 11/2014 | Shuros ............... A61B 5/04012 600/509 |
| 2014/0343388 | A1* | 11/2014 | Thakur ............... A61B 5/04011 600/374 |
| 2014/0343442 | A1 | 11/2014 | Thakur et al. |
| 2014/0371616 | A1 | 12/2014 | Narayan et al. |
| 2015/0065836 | A1 | 3/2015 | Thakur et al. |
| 2015/0366476 | A1 | 12/2015 | Laughner et al. |
| 2016/0073913 | A1 | 3/2016 | Francis et al. |
| 2016/0089050 | A1 | 3/2016 | Thakur et al. |

FOREIGN PATENT DOCUMENTS

| | | |
|---|---|---|
| CN | 102245091 A | 11/2011 |
| CN | 105307558 A | 2/2016 |
| EP | 2258263 B1 | 8/2012 |
| EP | 2996547 A1 | 3/2016 |
| GB | 13072111 | 5/2013 |
| JP | 2005131367 A | 5/2005 |
| JP | 4001959 B2 | 10/2007 |
| JP | 2007537823 A | 12/2007 |
| JP | 2009537252 A | 10/2009 |
| JP | 2012505047 A | 3/2012 |
| JP | 2013523345 A | 6/2013 |
| JP | 2014502556 A | 2/2014 |
| WO | WO0045700 A1 | 8/2000 |
| WO | 2006066324 A1 | 6/2006 |
| WO | 2007035306 A3 | 3/2007 |
| WO | 2007146864 A3 | 12/2007 |
| WO | 2008097767 A2 | 8/2008 |
| WO | 2009085108 A1 | 7/2009 |
| WO | 2009123819 A3 | 10/2009 |
| WO | 2010051183 A1 | 5/2010 |
| WO | 2010123637 A2 | 10/2010 |
| WO | 2010129095 A2 | 11/2010 |
| WO | 2011127211 A2 | 10/2011 |
| WO | 2011142931 A1 | 11/2011 |
| WO | 2011142932 A1 | 11/2011 |
| WO | 2012092016 A1 | 7/2012 |
| WO | 2012097059 A1 | 7/2012 |
| WO | 2012097067 A1 | 7/2012 |
| WO | 2012151008 A2 | 11/2012 |
| WO | 2013123549 A1 | 8/2013 |
| WO | 2014100464 A1 | 6/2014 |
| WO | 2014186684 A1 | 11/2014 |

OTHER PUBLICATIONS

Jadidi, Amir S. et al., "Functional Nature of Electrogram Fractionation Demonstrated by Left Atrial High-Density Mapping", Circulation: Arrhythmia and Electrophysiology, 5(1):32-42, Feb. 1, 2012.

Rogers, Jack M. et al., "Recurrent Wavefront Morphologies: A Method for Quantifying the Complexity of Epicardial Activation Patterns", Annals of Biomedical Engineering, 25(5):761-768, Sep. 1, 1997.

Sanders, Prashanthan et al., "Spectral Analysis Identifies Sites of High-Frequency Activity Maintaining Atrial Fibrillation in Humans", Circulation, 112(6):789-797, Aug. 9, 2005.

Etienne M. Aliot, et al. "EHRA/HRS Expert Consensus on Catheter Ablation of Ventricular Arrhythmias," European Society of Cardiology. The European Heart Rhythm Association, 11:771-817, 2009.

Deepak Bhakta, et al. "Principles of Electroanatomic Mapping," Indian Pacing and Electrophysiology Journal. Krannert Institute of Cardiology. Indianapolis, Indiana, 8(1):32-50, 2008.

Corinna B. Brunckorst, et al. "Identification of the Ventricular Tachycardia Isthmus After Infarction by Pace Mapping," Circulation Journal of the American Heart Association. Volume Circulation, American Heart Association. Dallas, Texas, 110:652-659, Aug. 2, 2004.

William G. Stevenson, et al. Journal of the American College of Cardiology. Fractionated Endocardial Electrograms are Associated With Slow Conduction in Humans: Evidence From Pace-Mapping, Los Angeles, California, 13(2):369-376, Feb. 1989.

Ken Okumura, et al. "Pathophysiology and Natural History Ventricular Tachycardia. Demonstration of the Presence of Slow Conduction During Sustained Ventricular Tachycardia in Man: Use of Transient Entrainment of the Tachycardia," Department of Medicine, Case Western Reserve University/University Hospitals of Cleveland, Ohio and the University of Alabama at Birmingham, 75(2):369-378. Feb. 1987.

Shiro Nakahara, et al. "Characterization of the Arrhythmogenic Substrate in Ischemic and Nonischemic Cardiomyopathy. Implications for Catheter Ablation of Hemodynamically Unstable Ventricular Tachycardia," Journal of the American College of Cardiology. Los Angeles, California, 55(21):2355-2365, May 25, 2010.

Takeshi Tsuchiya, et al. "Significance of Late Diastolic Potential Preceding Purkinje Potential in Verapamil-Sensitive Idiopathic Left Ventricular Tachycardia," American Heart Association. Japan, pp. 2408-2413, May 11, 1999.

Hong Cao, et al. "FEM Analysis of Predicting Electrode-Myocardium Contact From RF Cardiac Catheter Ablation System Impedance," IEEE Transactions on Biomedical Engineering. IEEE Engineering in Medicine and Biology Society. Madison, Wisconsin. 49(6):520-526, Jun. 2002.

Stevenson WG, et al. "Identifying sites for Catheter Ablation of Ventricular Tachycardia," PubMed NCBI. MeSH Terms, Abstract, Jun. 1992.

Jang-Zern Tsai, et al. "Dependence of Apparent Resistance of Four-Electrode Probes on Insertion Depth," IEEE Transactions on Biomedical Engineering. IEEE Engineering in Medicine and Biology Society. Madison, Wisconsin, 47(1):41-48, Jan. 2000.

Minglong Chen, et al. "Non-contact mapping and linear ablation of the left posterior fascicle during sinus rhythm in the treatment of idiopathic left ventricular tachycardia," European Society of Cardiology. vol. 7: pp. 138-144. Elsevier Ltd. China, 2005.

Jang-Zern Tsai, et al. "Error Analysis of Tissue Resistivity Measurement. IEEE Transactions on Biomedical Engineering," IEEE Engineering in Medicine and Biology Society. Madison, Wisconsin, 49(5):484-494, May 2002.

Ji-Qiang Hu, et al. "The Characteristics of Verapamil-sensitive Idiopathic left Ventricular Tachycardia combined with a left accessory pathway and the effect of radiofrequency catheter ablation," Clinical Research Electrophysiology and Ablation. The European Society of Cardiology. Beijing, China. pp. 704-708, Jun. 30, 2012.

Koonlawee Nademanee, et al. "How to perform Electrogram-guided Atrial Fibrillation Ablation," The Pacific Rim Electrophysiology Research Institute. Heart Rhythm Society. Inglewood, California, 3(8):981-984, Aug. 2006.

Feifan Ouyang, et al. "Electroanatomic Substrate of Idiopathic Left Ventricular Tachycardia: Unidirectional Block and Macroreentry Within the Purkinje Network," Circulation Journal of the American Heart Association. American Heart Association. Dallas, Texas. 105(10):462-469, 2002.

(56) References Cited

OTHER PUBLICATIONS

Quan Ni, et al. "A Novel Interpolation Method of Electric Potential Fields in the Heart during Excitation," Annals of Biomedical Engineering. Biomedical Engineering Society. Salt Lake City, Utah. vol. 26:597-607, 1998.
Jason NG, et al. "Understanding and Interpreting Dominant Frequency Analysis of AF Electrograms," J Cardiovasc Electrophysiol. Blackwell. Chicago, Illinois. 18(6):680-685, 2007.
Koonlawee Nademanee, et al. A New Approach for Catheter Ablation of Atrial Fibrillation: Mapping of the Electrophysiologic Substrate. Journal of the American College of Cardiology. Jun. 2, 2004. 43(11):2044-2053. Elsevier Inc. Inglewood, California; and Bangkok, Thailand.
Nademanee K, et al. "Catheter Ablation of Atrial Fibrillation guided by complex Fractionated Atrial Electrogram Mapping of Atrial Fibrillation Substrate," Pacific Rim Eltrophysiology Research Institute. Elsevier Ltd. Los Angeles, California. 55(3):404-408, May 2010.
Chen I-Ching, et al. "Radiofrequency Ablation Therapy in Concealed Left Free Wall Accessory Pathway With Decremental Conduction," The Cardiopulmonary and Critical Care Journal. CHEST. New York City, New York. pp. 107(1):40-45, Jan. 1995.
Prashanthan Sanders, et al. Spectral Analysis Identifies Sites of High-Frequency Activity Maintaining Atrial Fibrillation in Humans. Circulation Journal of the American Heart Association. The American Heart Association, Inc. Dallas, Texas. 112:789-797, Aug. 9, 2005.
William G. Stevenson, et al. "Recording Techniques of Clinical Electrophysiology," J Cardiovasc Electrophysiol. Blackwell. Boston, Massachusetts. 16(9)1017-1022, 2005.
Joseph B. Morton, et al. "Sensitivity and Specificity of Concealed Entrainment for the Identification of Critical Isthmus in the Atrium: Relationship to Rate, Anatomic Location and Antidromic Penetration," Journal of the American College of Cardiology. Elsevier Science Inc. Melbourne, Australia. 39(5):896-906. Mar. 6, 2002.
William G. Stevenson, et al. "Identification of Reentry Circuit Sites During Catheter Mapping and Radiofrequency Ablation of Ventricular Tachycardia Late After Myocardial Infarction," Circulation. American Heart Association. Los Angeles, California. 88(4):1646-1670, Oct. 1993.
International Search Report and Written Opinion issued in PCT/US2014/062876, mailed Feb. 11, 2015, 12 pages.
Barbaro, V., et. al. Measure of Synchronisation of Right Atrial Depolarisation Wavefronts During Atrial Fibrillation, Med. Biol. Eng, Comput., 40(1): 56-62, 2002.
Berkowitsch, Alexander et al., "Electrophysiological Heterogeneity of Atrial Fibrillation and Local Effect of Propafenone in the Human Right Atrium: Analysis Based of Symbolic dynamics", Journal of Interventional Cardiac Electrophysiology, Jun. 1, 2000, pp. 383-394.
Brodda, K., et al. A New Method for Detection of P Waves in Electrocardiograms. Signal Processing, 1(1): 15-25, 1979.
Ciaccio, Edward J. et al., "Identification of recurring patterns in fractionated atrial electrograms using new transform coefficients", Biomedical engineering Online, vol. 11, No. 1, Jan. 1, 2012, 19 pages.
Fitzgerald, Tamara N. et al., "Identification of Cardiac Rhythm Features by Mathematical Analysis of Vector Fields", IEEE Transactions on Biomedical Engineering, vol. 52, No. 1, Jan. 2005, pp. 19-29.
Holm, Magnus et al. A New Method for Analysis of Atrial Activation During Chronic Atrial Fibrillation in Man. IEEE Transactions on Biomedical Engineering, 43(2): 198-210, Feb. 1996.
Houben, Richard P.M. et al., "Processing Intracardiac Electrograms in Atrial Fibrillation", Diagosis of Electropathological Substrate of AF, IEEE Engineering in Medicine and Biology Magazine, Nov./Dec. 2006, pp. 40-51.
International Preliminary Report on Patentability issued in PCT/US2013/076667, mailed Jul. 2, 2015, 9 pages.
International Search Report and Written Opinion issued in PCT/US2014/038357, mailed Sep. 1, 2014, 11 pages.
International Search Report and Written Opinion issued in PCT/US2013/076667, mailed Mar. 20, 2014, 14 pages.
International Search Report and Written Opinion issued in PCT/US2015/036746, mailed Sep. 1, 2015, 12 pages.
International Search Report and Written Opinion issued in PCT/US2014/053147, mailed Nov. 7, 2014, 12 pages.
Marbroukeh Nizar R. et al., "Taxonomy of Sequenial Pattern Mining Algorithms", ACM Computing Surveys, vol. 43, No. 1, Nov. 1, 2010, pp. 1-41.
Masse, Stephane et al., "Wave similarity of human ventricular fibrillation from bipolar electrograms", Europace, vol. 9, No. 1, Jan. 1, 2007, 10 pages.
Houben, R. P. M., et, al. Processing of intracardiac Electrograms in Atrial Fibrillation: Diagnosis of Electropathological Substrate of AF. IEEE Engineering in Medicine and Biology Magazine, 25(6):40-51, Nov. 1, 2006.
International Preliminary Report on Patentability issued in PCT/US2014/038357, mailed Nov. 26, 2015, 8 pages.
International Preliminary Report on Patentability issued in PCT/US2014/053147, mailed Mar. 10, 2016, 9 pages.
International Preliminary Report on Patentability issued in PCT/US2014/062876, mailed May 12, 2016, 9 pages.
International Preliminary Report on Patentability issued in PCT/US2015/036746, dated Dec. 20, 2016, 8 pages.
Masse, Stephane, et al. "Ventricular Fibrillation in Myopathic Human Hearts: Mechanistic Insights From in Vivo Global Endocardial and Epicardial Mapping." Am. J. Physiol. Heart Circ. Physiol. 292:H2589-H2597, 2007.

\* cited by examiner

MEDICAL DEVICE FOR HIGH RESOLUTION MAPPING USING LOCALIZED MATCHING

CROSS-REFERENCE TO RELATED APPLICATIONS

This application claims priority under 35 U.S.C. §119 to U.S. Provisional Application Ser. No. 61/898,312, filed Oct. 31, 2013, the entirety of which is incorporated herein by reference.

TECHNICAL FIELD

The present disclosure pertains to medical devices, and methods for manufacturing medical devices. More particularly, the present disclosure pertains to elongated intracorporeal medical devices including a tubular member connected with other structures, and methods for manufacturing and using such devices.

BACKGROUND

A wide variety of intracorporeal medical devices have been developed for medical use, for example, intravascular use. Some of these devices include guidewires, catheters, and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

BRIEF SUMMARY

This disclosure provides design, material, manufacturing method, and use alternatives for medical devices. A medical device is disclosed. The medical device comprises:
 a catheter shaft with a plurality of electrodes coupled thereto;
 a processor, wherein the processor is capable of:
 collecting a first set of signals from a first location;
 collecting a second set of signals from a second location;
 characterizing the first set of signals over a first time period;
 characterizing the second set of signals over a second time period;
 comparing the first set of signals to the second set of signals; and
 matching a first signal from the first set of signals with a second signal from the second set of signals.

Alternatively or additionally to any of the embodiments above, collecting the first and second set of signals includes sensing a change in electrical potential over the first and second time periods.

Alternatively or additionally to any of the embodiments above, using one or more of the plurality of electrodes in sensing a change in electrical potential over the first or second time periods.

Alternatively or additionally to any of the embodiments above, wherein collecting the first or second signals includes disposing the plurality of electrodes in the heart.

Alternatively or additionally to any of the embodiments above, wherein the plurality of electrodes are disposed on a basket electrode structure.

Alternatively or additionally to any of the embodiments above, wherein the plurality of electrodes are coupled to the processor.

Alternatively or additionally to any of the embodiments above, wherein characterizing the first set of signals includes generating a first unique signal pattern and wherein characterizing the second set of signals includes generating a second unique signal pattern.

Alternatively or additionally to any of the embodiments above, wherein characterizing the first set of signals includes determining a first number of occurrences of the first unique signal pattern across the first time period.

Alternatively or additionally to any of the embodiments above, wherein characterizing the first set of signals further comprises calculating a first frequency of the first unique signal pattern within the first time period, wherein the first frequency of the first unique signal pattern is determined by dividing the first number of occurrences of the first unique signal pattern by the first time period.

Alternatively or additionally to any of the embodiments above, wherein characterizing the second set of signals includes determining a second number of occurrences of the second unique signal pattern within the second time period.

Alternatively or additionally to any of the embodiments above, wherein characterizing the second set of signals further comprises calculating a second frequency of the second unique signal pattern within the second time period, wherein the second frequency of the second unique signal pattern is determined by dividing the second number of occurrences of the second unique signal pattern by the second time period.

Alternatively or additionally to any of the embodiments above, wherein matching a first signal from the first set of signals with a second signal from the second set of signals includes matching the first frequency with the second frequency.

Alternatively or additionally to any of the embodiments above, comprising matching additional unique signal patterns and using the matched signal patterns to generate a high resolution map.

Alternatively or additionally to any of the embodiments above, wherein matching the first signal from the first set of signals with the second signal from the second set of signals includes aligning the first unique signal pattern with the second unique signal pattern.

Alternatively or additionally to any of the embodiments above, wherein aligning the first unique signal pattern with the second unique signal pattern includes identifying a region of overlap between the first unique signal pattern and the second unique signal pattern.

Alternatively or additionally to any of the embodiments above, wherein aligning the first unique signal pattern with the second unique signal pattern includes determining and matching a first activity gradient of the first unique signal pattern with a second activity gradient of the second unique signal pattern.

Alternatively or additionally to any of the embodiments above, wherein characterizing the first set of signals includes determining a first number of occurrences of the first unique signal pattern within the first time period.

Alternatively or additionally to any of the embodiments above, wherein characterizing the first set of signals further comprises calculating a first frequency of the first unique signal pattern within the first time period, wherein the frequency of the first unique signal pattern is determined by dividing the first number of occurrences of the first unique signal pattern by the first time period.

Alternatively or additionally to any of the embodiments above, wherein characterizing the second set of signals includes determining a second number of occurrences of the second unique signal pattern within the second time period.

Alternatively or additionally to any of the embodiments above, wherein characterizing the second set of signals further comprises calculating a second frequency of the second unique signal pattern within the second time period, wherein the second frequency of the second unique signal pattern is determined by dividing the second number of occurrences of the second unique signal pattern by the second time period.

Alternatively or additionally to any of the embodiments above, wherein matching a first signal from the first set of signals with a second signal from the second set of signals includes matching the first frequency with the second frequency.

Alternatively or additionally to any of the embodiments above, wherein matching additional unique signal patterns and using the matched signal patterns to generate a high resolution map.

Alternatively or additionally to any of the embodiments above, wherein matching the first signal from the first set of signals with a second signal from the second set of signals includes matching the first unique signal pattern and the second unique signal pattern to a signal template.

Alternatively or additionally to any of the embodiments above, wherein characterizing the first set of signals includes determining a first number of occurrences of the first unique signal pattern within the first time period.

Alternatively or additionally to any of the embodiments above, wherein characterizing the first set of signals further comprises calculating a first frequency of the first unique signal pattern within the first time period, wherein the frequency of the first unique signal pattern is determined by dividing the first number of occurrences of the first unique signal pattern by the first time period.

Alternatively or additionally to any of the embodiments above, wherein characterizing the second set of signals includes determining a second number of occurrences of the second unique signal pattern within the second time period.

Alternatively or additionally to any of the embodiments above, characterizing the second set of signals further comprises calculating a second frequency of the second unique signal pattern within the second time period, wherein the second frequency of the second unique signal pattern is determined by dividing the second number of occurrences of the second unique signal pattern by the second time period.

Alternatively or additionally to any of the embodiments above, wherein matching a first signal from the first set of signals with a second signal from the second set of signals includes matching the first frequency with the second frequency.

Alternatively or additionally to any of the embodiments above, further comprising matching additional unique signal patterns and using the matched signal patterns to generate a high resolution map.

Alternatively or additionally to any of the embodiments above, the first time period is the same duration as the second time period.

Alternatively or additionally to any of the embodiments above, wherein the first time period is different from the second time period.

Alternatively or additionally to any of the embodiments above, further comprising collecting one or more sets of data at one or more additional locations over one or more additional time periods.

A method for delivering a medical device is disclosed. The method comprises:

delivering the medical mapping device of any one of claims 1-20 into the heart of a patient.

A method for delivering a medical device is disclosed. The method comprises:

collecting a first set of signals from a first location;

collecting a second set of signals from a second location;

characterizing the first set of signals over a first time period;

characterizing the second set of signals over a second time period;

comparing the first set of signals to the second set of signals; and matching a first signal from the first set of signals with a second signal from the second set of signals.

Alternatively or additionally to any of the embodiments above, wherein collecting the first and second set of signals includes sensing a change in electrical potential over the first and second time periods.

Alternatively or additionally to any of the embodiments above, further comprising using one or more of the plurality of electrodes in sensing a change in electrical potential over the first or second time periods.

Alternatively or additionally to any of the embodiments above, wherein collecting the first or second signals includes disposing the plurality of electrodes in the heart.

Alternatively or additionally to any of the embodiments above, wherein the plurality of electrodes are disposed on a basket electrode structure.

Alternatively or additionally to any of the embodiments above, wherein the plurality of electrodes are coupled to the processor.

Alternatively or additionally to any of the embodiments above, wherein characterizing the first set of signals includes generating a first unique signal pattern and wherein characterizing the second set of signals includes generating a second unique signal pattern.

Alternatively or additionally to any of the embodiments above, wherein characterizing the first set of signals includes determining a first number of occurrences of the first unique signal pattern across the first time period.

Alternatively or additionally to any of the embodiments above, wherein characterizing the first set of signals further comprises calculating a first frequency of the first unique signal pattern within the first time period, wherein the first frequency of the first unique signal pattern is determined by dividing the first number of occurrences of the first unique signal pattern by the first time period.

Alternatively or additionally to any of the embodiments above, wherein characterizing the second set of signals includes determining a second number of occurrences of the second unique signal pattern within the second time period.

Alternatively or additionally to any of the embodiments above, wherein characterizing the second set of signals further comprises calculating a second frequency of the second unique signal pattern within the second time period, wherein the second frequency of the second unique signal pattern is determined by dividing the second number of occurrences of the second unique signal pattern by the second time period.

Alternatively or additionally to any of the embodiments above, wherein matching a first signal from the first set of signals with a second signal from the second set of signals includes matching the first frequency with the second frequency.

Alternatively or additionally to any of the embodiments above, further comprising matching additional unique signal patterns and using the matched signal patterns to generate a high resolution map.

Alternatively or additionally to any of the embodiments above, wherein matching the first signal from the first set of signals with the second signal from the second set of signals includes aligning the first unique signal pattern with the second unique signal pattern.

Alternatively or additionally to any of the embodiments above, wherein aligning the first unique signal pattern with the second unique signal pattern includes identifying a region of overlap between the first unique signal pattern and the second unique signal pattern.

Alternatively or additionally to any of the embodiments above, wherein aligning the first unique signal pattern with the second unique signal pattern includes determining and matching a first activity gradient of the first unique signal pattern with a second activity gradient of the second unique signal pattern.

Alternatively or additionally to any of the embodiments above, wherein characterizing the first set of signals includes determining a first number of occurrences of the first unique signal pattern within the first time period.

Alternatively or additionally to any of the embodiments above, wherein characterizing the first set of signals further comprises calculating a first frequency of the first unique signal pattern within the first time period, wherein the frequency of the first unique signal pattern is determined by dividing the first number of occurrences of the first unique signal pattern by the first time period.

Alternatively or additionally to any of the embodiments above, wherein characterizing the second set of signals includes determining a second number of occurrences of the second unique signal pattern within the second time period.

Alternatively or additionally to any of the embodiments above, wherein characterizing the second set of signals further comprises calculating a second frequency of the second unique signal pattern within the second time period, wherein the second frequency of the second unique signal pattern is determined by dividing the second number of occurrences of the second unique signal pattern by the second time period.

Alternatively or additionally to any of the embodiments above, wherein matching a first signal from the first set of signals with a second signal from the second set of signals includes matching the first frequency with the second frequency.

Alternatively or additionally to any of the embodiments above, further comprising matching additional unique signal patterns and using the matched signal patterns to generate a high resolution map.

Alternatively or additionally to any of the embodiments above, wherein matching the first signal from the first set of signals with a second signal from the second set of signals includes matching the first unique signal pattern and the second unique signal pattern to a signal template.

Alternatively or additionally to any of the embodiments above, wherein characterizing the first set of signals includes determining a first number of occurrences of the first unique signal pattern within the first time period.

Alternatively or additionally to any of the embodiments above, wherein characterizing the first set of signals further comprises calculating a first frequency of the first unique signal pattern within the first time period, wherein the frequency of the first unique signal pattern is determined by dividing the first number of occurrences of the first unique signal pattern by the first time period.

Alternatively or additionally to any of the embodiments above, wherein characterizing the second set of signals includes determining a second number of occurrences of the second unique signal pattern within the second time period.

Alternatively or additionally to any of the embodiments above, wherein characterizing the second set of signals further comprises calculating a second frequency of the second unique signal pattern within the second time period, wherein the second frequency of the second unique signal pattern is determined by dividing the second number of occurrences of the second unique signal pattern by the second time period.

Alternatively or additionally to any of the embodiments above, wherein matching a first signal from the first set of signals with a second signal from the second set of signals includes matching the first frequency with the second frequency.

Alternatively or additionally to any of the embodiments above, further comprising matching additional unique signal patterns and using the matched signal patterns to generate a high resolution map.

Alternatively or additionally to any of the embodiments above, wherein the first time period is the same duration as the second time period.

Alternatively or additionally to any of the embodiments above, wherein the first time period is different from the second time period.

Alternatively or additionally to any of the embodiments above, further comprising collecting one or more sets of data at one or more additional locations over one or more additional time periods.

A method for delivering a medical device is disclosed. The method comprises:

providing a catheter having a first electrode and a plurality of additional electrodes adjacent to the first electrode;

sensing one or more signals over a time period with the first electrode and the with the additional electrodes;

calculating one or more latencies between the first electrode and one or more of the plurality of electrodes over the time period;

using the one or more latencies to determine one or more directions of the one or more signals between the first electrode and one or more of the plurality of electrodes; and determining a dominant direction signal from the one or more directions.

Alternatively or additionally to any of the embodiments above, wherein calculating one or more latencies includes determining the position of the plurality of electrodes relative to a fixed coordinate system.

Alternatively or additionally to any of the embodiments above, wherein determining a dominant direction signal includes determining a sum of the one or more directions of the one or more signals.

Alternatively or additionally to any of the embodiments above, wherein the sum includes number of occurrences of the one or more directions of the one or more signals.

Alternatively or additionally to any of the embodiments above, wherein the determining a dominant direction signal includes determining a frequency, wherein the frequency is determined by dividing the sum by the time period.

Alternatively or additionally to any of the embodiments above, further comprising displaying the dominant direction on a display.

Alternatively or additionally to any of the embodiments above, wherein displaying the dominant direction includes displaying an arrow.

Alternatively or additionally to any of the embodiments above, wherein displaying the arrow includes lengthening the arrow.

Alternatively or additionally to any of the embodiments above, wherein displaying the arrow includes widening the arrow.

Alternatively or additionally to any of the embodiments above, wherein displaying the arrow includes thickening the arrow.

BRIEF DESCRIPTION OF THE DRAWINGS

The disclosure may be more completely understood in consideration of the following detailed description in connection with the accompanying drawings, in which.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the invention.

Mapping the electrophysiology of heart rhythm disorders often involves the introduction of a constellation catheter or other mapping/sensing device having a plurality of sensors into a cardiac chamber. The sensors detect the electric activity of the heart at sensor locations. It may be desirable to have the electric activity processed into and displayed as electrogram signals that accurately represent cellular excitation through cardiac tissue relative to the sensor locations. A processing system may then analyze and output the signal to a display device. The physician may use the displayed information to perform a diagnostic procedure. However, in some cases the sensing electrodes may fail to accurately detect electrical activity of heart. For example, the sensors may fail entirely to detect a signal or they may detect far-field electrical activity and/or electrical artifacts.

The processing system may be configured to detect a variety of activation signals generated by the electrical activity of the myocardial tissue and sensed by adjacent electrodes. However, a relatively limited number of electrodes on a constellation catheter or other mapping/sensing device may limit the resolution of the activation pattern sensing. Therefore, it may be desirable to reduce the total number of electrodes and/or the spacing between electrodes and collect electrical signal data from smaller, focused cardiac locations. Further, reducing the distance between electrodes may allow for the collection of high-resolution data. However, this high-resolution data may only be collected from small, localized cardiac regions. The methods and systems disclosed herein are designed to overcome at least some of the limitations of low-resolution standard activity mapping. For example, some of the methods disclosed herein may include collecting and combining high-resolution data from localized regions to create high-resolution maps of cardiac chambers. Other methods and medical devices are also disclosed.

Figure 1:
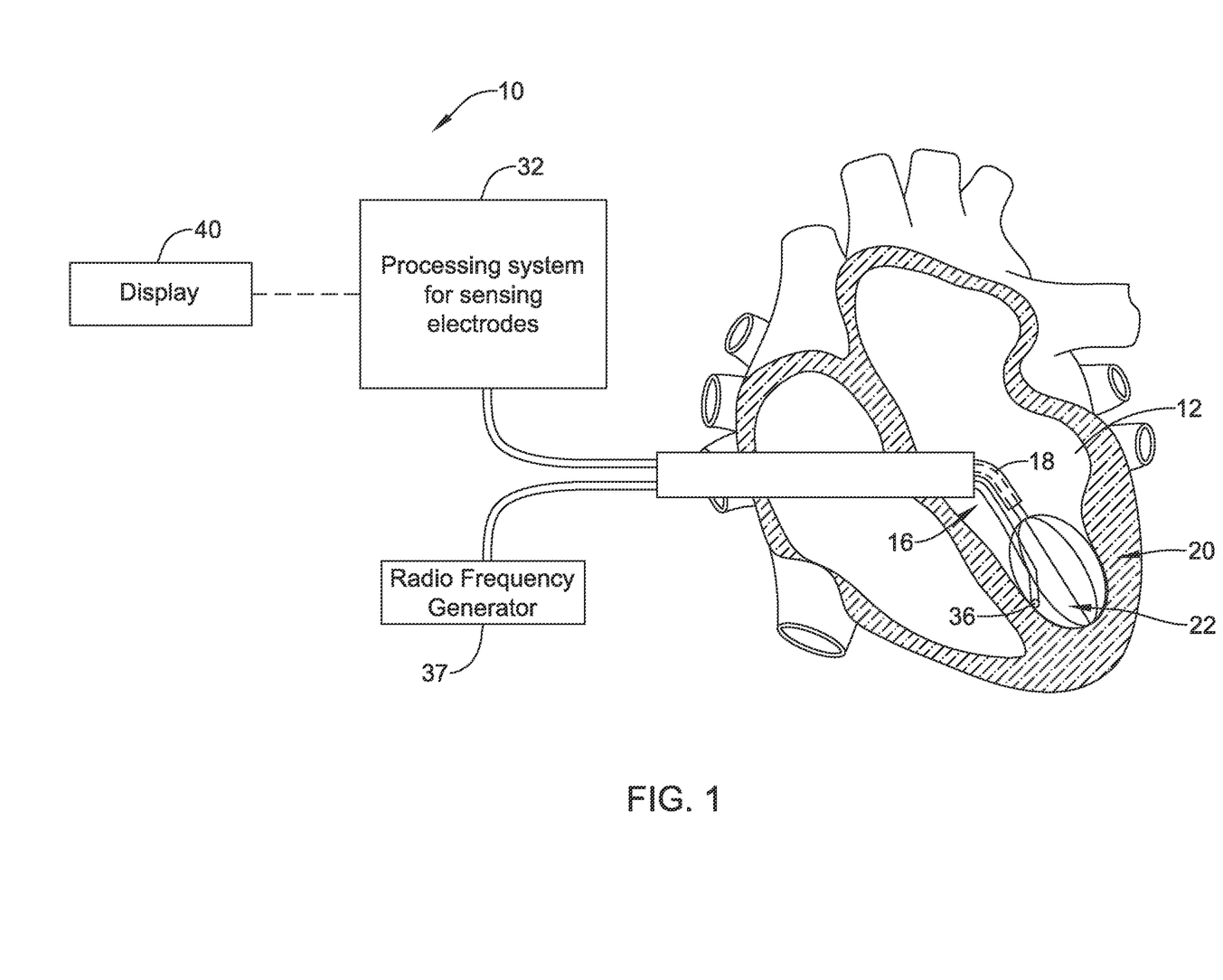
FIG. 1 is a schematic view of an embodiment of a catheter system for accessing a targeted tissue region in the body for diagnostic and therapeutic purposes.

FIG. 1 is a schematic view of a system 10 for accessing a targeted tissue region in the body for diagnostic and/or therapeutic purposes. FIG. 1 generally shows the system 10 deployed in the left atrium of the heart. Alternatively, system 10 can be deployed in other regions of the heart, such as the left ventricle, right atrium, or right ventricle. While the illustrated embodiment shows the system 10 being used for ablating myocardial tissue, the system 10 (and the methods described herein) may alternatively be configured for use in other tissue ablation applications, such as procedures for ablating tissue in the prostrate, brain, gall bladder, uterus, nerves, blood vessels and other regions of the body, including body regions not typically accessed by a catheter.

The system 10 may include a mapping probe 14 and an ablation probe 16. In FIG. 1, each is separately introduced into the selected heart region 12 through a vein or artery (e.g., the femoral vein or artery) through suitable percutaneous access. Alternatively, the mapping probe 14 and ablation probe 16 may be assembled in an integrated structure for simultaneous introduction and deployment in the heart region 12.

The mapping probe 14 may have a flexible catheter body 18. The distal end of the catheter body 18 may carry a three-dimensional multiple electrode structure 20. In the illustrated embodiment, the structure 20 takes the form of a basket defining an open interior space 22 (see FIG. 2), although other multiple electrode structures could be used wherein the geometry of the electrode structure and electrode locations may be known. The multiple electrode structure 20 carries a plurality of mapping electrodes 24 (not explicitly shown on FIG. 1, but shown on FIG. 2) each having an electrode location and channel. Each electrode 24 may be configured to sense intrinsic physiological activity in the anatomical region. In some embodiments, the electrodes 24 may be configured to detect activation signals of the intrinsic physiological activity within the anatomical structure, e.g., the activation times of cardiac activity.

Figure 2:
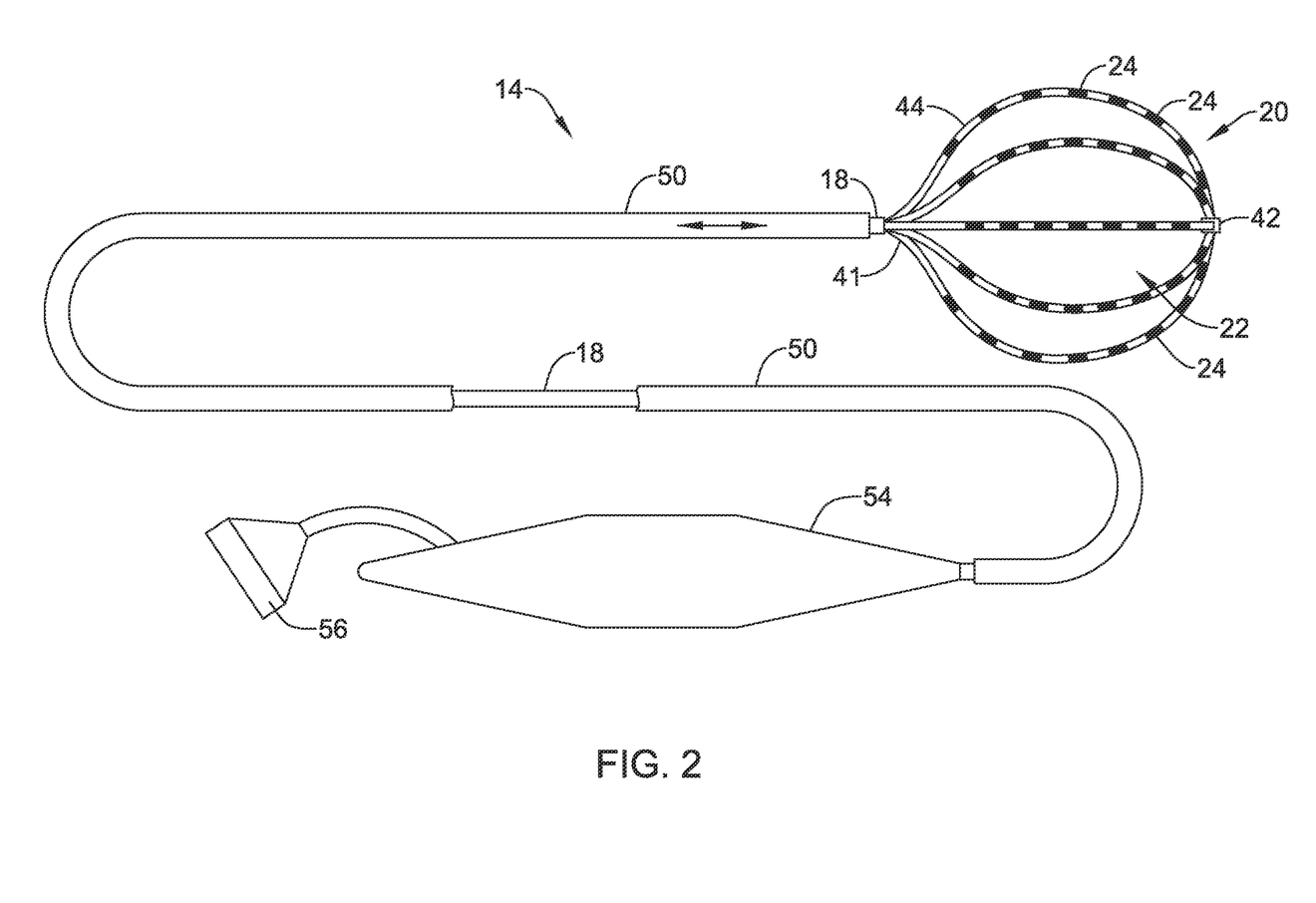
FIG. 2 is a schematic view of an embodiment of a mapping catheter having a basket functional element carrying structure for use in association with the system of FIG. 1.

The electrodes 24 may be electrically coupled to a processing system 32. A signal wire (not shown) may be electrically coupled to each electrode 24 on the basket structure 20. The wires extend through the body 18 of the probe 14 and electrically couple each electrode 24 to an input of the processing system 32, as will be described later in greater detail. The electrodes 24 sense intrinsic electrical activity in the anatomical region, e.g., myocardial tissue. The sensed activity, e.g. activation signals, is processed by the processing system 32 to assist the physician by generating an anatomical map, e.g., a vector field map, to identify the site or sites within the heart appropriate for a diagnostic and/or treatment procedure, e.g. an ablation procedure. For example, the processing system 32 may identify a near-field signal component, i.e. activation signals originating from cellular tissue adjacent to the mapping electrode 24, or from an obstructive far-field signal component, i.e. activation signals originating from non-adjacent tissue. For example, the near-field signal component may include activation signals originating from atrial myocardial tissue whereas the far-field signal component may include activation signals originating from ventricular myocardial tissue. The near-field activation signal component may be further analyzed to find the presence of a pathology and to determine a location suitable for ablation for treatment of the pathology, e.g., ablation therapy.

The processing system 32 includes dedicated circuitry (e.g., discrete logic elements and one or more microcontrollers; application-specific integrated circuits (ASICs); or specially configured programmable devices, such as, for example, programmable logic devices (PLDs) or field programmable gate arrays (FPGAs)) for receiving and/or processing the acquired activation signals. In some embodiments, the processing system 32 includes a general purpose microprocessor and/or a specialized microprocessor (e.g., a digital signal processor, or DSP, which may be optimized for processing activation signals) that executes instructions to receive, analyze and display information associated with the received activation signals. In such implementations, the processing system 32 can include program instructions, which when executed, perform part of the signal processing. Program instructions can include, for example, firmware, microcode or application code that is executed by microprocessors or microcontrollers. The above-mentioned implementations are merely exemplary. Other program instructions are contemplated.

In some embodiments, the processing system 32 may be configured to measure the intrinsic electrical activity in the myocardial tissue adjacent to the electrodes 24. For example, in some embodiments, the processing system 32 is configured to detect intrinsic electrical activity associated with a dominant rotor or divergent activation pattern in the anatomical feature being mapped. For example, dominant rotors and/or divergent activation patterns may have a role in the initiation and maintenance of atrial fibrillation, and ablation of the rotor path, rotor core, and/or divergent foci may be effective in terminating the atrial fibrillation. In either situation, the processing system 32 processes the sensed activation signals to generate a display of relevant characteristics, such as an APD map, a vector field map, a contour map, a reliability map, an electrogram, a cardiac action potential and the like. The relevant characteristics may be used by the physician to identify a site suitable for ablation therapy.

The ablation probe 16 may include a flexible catheter body 34 that carries one or more ablation electrodes 36. The one or more ablation electrodes 36 may be electrically connected to a radio frequency generator (RF) 37 that may be configured to deliver ablation energy to the one or more ablation electrodes 36. The ablation probe 16 may be movable with respect to the anatomical feature to be treated, as well as the structure 20. The ablation probe 16 may be positionable between or adjacent to electrodes 24 of the structure 20 as the one or more ablation electrodes 36 are positioned with respect to the tissue to be treated.

The processing system 32 may output to a device 40 the display of relevant characteristics for viewing by a physician. In the illustrated embodiment, device 40 is a CRT, LED, or other type of display, or a printer. The device 40 may present the relevant characteristics in a format most useful to the physician. In addition, the processing system 32 may generate position-identifying output for display on the device 40 that aids the physician in guiding the ablation electrode(s) 36 into contact with tissue at the site identified for ablation.

FIG. 2 illustrates an embodiment of the mapping catheter 14 including electrodes 24 at the distal end and may be suitable for use in the system 10 shown in FIG. 1. The mapping catheter 14 has a flexible catheter body 18, the distal end of which carries the three dimensional structure 20 configured to carry the mapping electrodes or sensors 24. The mapping electrodes 24 sense intrinsic electrical activity, e.g., activation signals, in the myocardial tissue, the sensed activity is then processed by the processing system 32 to assist the physician in identifying the site or sites having a heart rhythm disorder or other myocardial pathology via generated and displayed relevant characteristics. This information may be used to determine an appropriate location for applying appropriate therapy, such as ablation, to the identified sites, and/or to aid in navigation of the one or more ablation electrodes 36 to the identified sites.

The illustrated three-dimensional structure 20 comprises a base member 41 and an end cap 42 between which flexible splines 44 generally extend in a circumferentially spaced relationship. As discussed above, the three dimensional structure 20 takes the form of a basket defining an open interior space 22. In some embodiments, the splines 44 are made of a resilient inert material, such as Nitinol metal or silicone rubber, and are connected between the base member 41 and the end cap 42 in a resilient, pretensed condition, to bend and conform to the tissue surface they contact. In the illustrated embodiment, eight splines 44 form the three dimensional structure 20. Additional or fewer splines 44 could be used in other embodiments. As illustrated, each spline 44 carries eight mapping electrodes 24. Additional or fewer mapping electrodes 24 could be disposed on each spline 44 in other embodiments of the three dimensional structure 20. In the illustrated embodiment, the three dimensional structure 20 is relatively small (e.g., 40 mm or less in diameter). In alternative embodiments, the three dimensional structure 20 is even smaller or larger (e.g., 40 mm in diameter or greater).

A slidable sheath 50 may be movable along the major axis of the catheter body 18. Moving the sheath 50 forward (i.e., toward the distal end) causes the sheath 50 to move over the three dimensional structure 20, thereby collapsing the structure 20 into a compact, low profile condition suitable for introduction into and/or removal from an interior space of an anatomical structure, such as, for example, the heart. In contrast, moving the sheath 50 rearward (i.e., toward the proximal end) exposes the three dimensional structure 20, allowing the structure 20 to elastically expand and assume the pretensed position illustrated in FIG. 2.

A signal wire (not shown) is electrically coupled to each mapping electrode 24. The wires extend through the body 18 of the mapping catheter 20 into a handle 54, in which they are coupled to an external connector 56, which may be a multiple pinconnector. The connector 56 electrically couples the mapping electrodes 24 to the processing system 32. Further details on mapping systems and methods for processing signals generated by the mapping catheter are discussed in U.S. Pat. No. 6,070,094, entitled "Systems and Methods for Guiding Movable Electrode Elements within Multiple Electrode Structure," U.S. Pat. No. 6,233,491, entitled "Cardiac Mapping and Ablation Systems," and U.S. Pat. No. 6,735,465, entitled "Systems and Processes for Refining a Registered Map of a Body Cavity," the disclosures of which are hereby expressly incorporated herein by reference.

Figure 3:
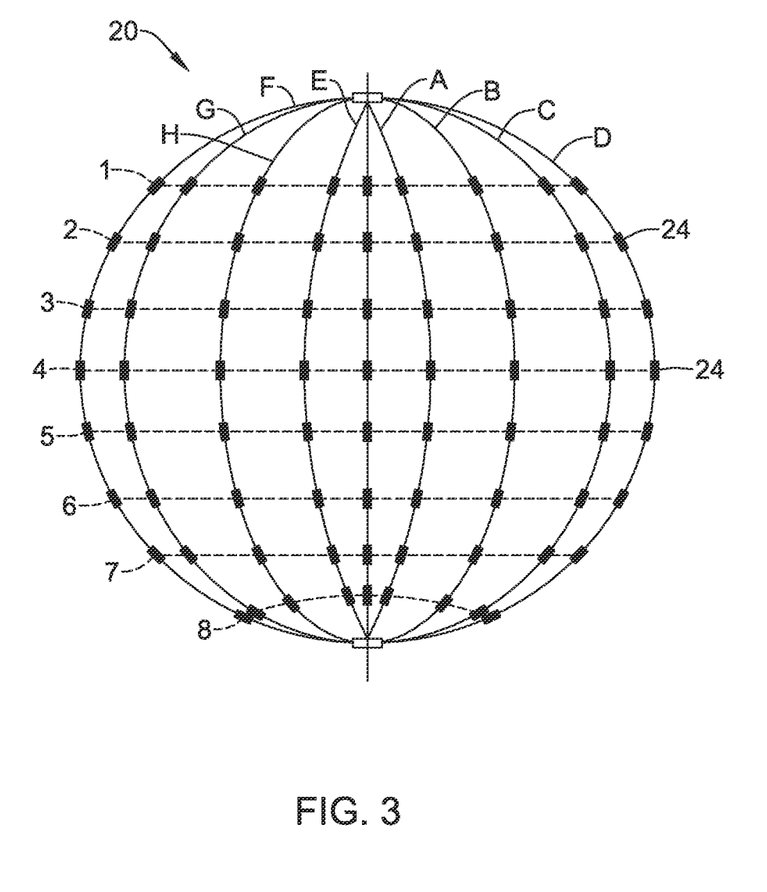
FIG. 3 is a schematic view of an embodiment of the basket functional element including a plurality of mapping electrodes.

To illustrate the operation of the system 10, FIG. 3 is a schematic side view of an embodiment of the basket structure 20 including a plurality of mapping electrodes 24. In the illustrated embodiment, the basket structure includes 64 mapping electrodes 24. The mapping electrodes 24 are disposed in groups of eight electrodes (labeled 1, 2, 3, 4, 5, 6, 7, and 8) on each of eight splines (labeled A, B, C, D, E, F, G, and H). While an arrangement of sixty-four mapping electrodes 24 is shown disposed on a basket structure 20, the mapping electrodes 24 may alternatively be arranged in different numbers, on different structures, and/or in different positions. In addition, multiple basket structures can be deployed in the same or different anatomical structures to simultaneously obtain signals from different anatomical structures.

After the basket structure 20 is positioned adjacent to the anatomical structure to be treated (e.g. left atrium, left ventricle, right atrium, or right ventricle of the heart), the processing system 32 is configured to record the activation signals from each electrode 24 channel related to physiological activity of the anatomical structure, i.e. the electrodes 24 measure electrical activation signals intrinsic to the physiology of the anatomical structure. The activation signals of physiological activity can be sensed in response to intrinsic physiological activity or based on a predetermined pacing protocol instituted by at least one of the plurality of electrodes 24.

The arrangement, size, spacing and/or location of electrodes along a constellation catheter or other mapping/sensing device, in combination with the geometry of the targeted anatomical structure, may contribute to the accuracy with which sensing electrodes collect and transmit electrical activity of targeted cellular tissue. For example, if the total number of electrodes and/or the distance between electrodes is decreased on a constellation catheter or other sensing device, the resolution of the data acquired from the catheter/device may be reduced. Further, the resolution of activation signals sensed by mapping electrodes 24 may vary depending on the particular spacing, arrangement and position of the mapping electrodes 24 on basket structure 20 and/or the position of the basket structure 20 within a particular cardiac chamber. FIG. 3 illustrates 64 electrodes positioned such that the spacing may correlate to a particular resolution of sensed activation signals. However, it can be appreciated that changing the relative position, shape, arrangement and/or distance between mapping electrodes 24 may correlate to a different degree of resolution. Additionally, decreasing the overall size, shape and/or position of basket structure 20 may also correlate to a change in the resolution of sensed activation signals. Further, changing both the relative size, spacing, position, shape and/or arrangement of both the mapping electrodes 24 and the basket structure 20 may result in a different resolution of sensed activation signals.

As indicated, reducing the size and/or dimensions of multiple electrode structure 20 may reduce the space between mapping electrodes 24. Further, reducing the size of multiple electrode structure 20 may result in a reduced "target area" of cellular tissue that may be mapped during a particular time period. However, reducing the spacing between mapping electrodes 24 may increase the resolution of sensed electrical activity, e.g. activation signals. Therefore, in some embodiments it may be desirable to reduce the overall size and/or dimensions of multiple electrode structure 20 despite the reduction in the target area. The smaller target area may have an increased resolution (over a smaller area), and therefore, it may be desirable to combine "higher resolution" electrical activity data from several reduced target area locations using the smaller multiple electrode structure. Further, a high-resolution "global" cardiac chamber map may be generated by combining several small high-resolution maps. Therefore, a need may exist for techniques to combine several local, high-resolution cardiac maps into a single, global high-resolution cardiac map.

Matching a first signal from a first set of signals with a second signal from the second set of signals to generate a high resolution map of electrical activation data collected from localized regions within a cardiac chamber may include matching signals according to the frequency at which particular activation patterns in the regions occur over a given time period. As stated, the processing system 32 may be configured to measure the intrinsic electrical activity in the myocardial tissue adjacent to the mapping electrodes 24. Further, the processing system 32 may be configured to detect intrinsic electrical activity associated with multiple "unique" activation patterns of cellular wave excitation propagations, e.g. a dominant rotor or divergent activation pattern. Example representations of activation patterns may include, but are not limited to, vector field patterns, contour maps, isochrones lines, activation potential displays, and/or phase maps. Dominant rotor or divergent activation patterns illustrate one of several example unique patterns of intrinsic electrical activity that may be detected by processing system 32. Further, an electrode structure 20 connected to processing system 32 may sense multiple unique activity patterns occurring over a time period. The processing system 32 may be able to distinguish and categorize each unique signal pattern occurring at a particular cardiac location. Additionally, the processing system 32 may be able to determine each unique signal pattern occurrence at a particular cardiac location over a particular time period. Therefore, the "frequency" or prevalence of each unique signal pattern in a given location may be calculated by dividing the number of each unique signal pattern occurrence over a particular time period. Frequencies for unique signal patterns may be calculated for unique signal patterns sensed in any number of locations in a cardiac chamber. Further, the locations at which sampling occurs may or may not overlap and the time period for which multiple electrode structure 20 collects (i.e. samples) the electrical activity can be the either the same or different across multiple cardiac locations. However, the time period for which sampling occurs may be long enough to construct prevalence of the unique signal patterns but short enough such that electrical activity can be considered stable across the cellular activation sequences. Example time periods may include 1 to 2 minutes, 1 to 5 minutes, 1 to 10 minutes, 5 to 10 minutes or 5 to 20 minutes.

The calculated frequencies may be compared across multiple sampling locations within the targeted region (i.e. cardiac chamber). For example, a multiple electrode structure 20 may be placed in a cardiac chamber at a first location and may sense data for a first period of time. The sensed activation signals may be collected, categorized unique signal patterns (e.g. collected and characterized at the first location), and the frequencies may be calculated. The multiple electrode structure 20 may then be placed in a cardiac chamber at a second location and may sense data for a second period of time. The second position may or may not overlap with the first position. The first time period may or may not be the same as the second time period. Sensed activation signals may be collected, categorized as unique signal patterns (e.g. collected and characterized at the second location), and frequencies may be calculated. The frequencies calculated at the first location may be compared to the frequencies calculated at the second location.

For the purpose of this disclosure, it is assumed that unique signal patterns that occur at or about the same frequency are part of the same activation signal. Further, unique signal patterns at a first location may be matched with unique signal patterns at a second location based on the similarity of their respective frequencies. The similarity of the frequencies may be assessed by determining if the "similar" frequencies fall within a threshold correlation value. The correlation value may be used to calculate the range of frequencies that may be considered "matched" to a target frequency. The correlation value may be a numerical percentage. For example, the correlation value may be set to 10% (e.g., within about 10% or less). Therefore, an example frequency of 50 at a first location may be considered matched to another example frequency of 45-55 at another location. While a correlation value of 10% may be suitable, this is not intended to be limiting. Other correlation values may be utilized such as about 0.25-20%, or about 1-20%, or about 2-10%, or about 2-20%, or about 5-10%, or within about 20% or less, or within about 15% or less, or within about 10% or less, or within about 5% or less.

After matching the frequencies from the first and second locations, the corresponding unique signal patterns correlating to these frequencies may be matched. Further, unique signal patterns from multiple locations in the cardiac chamber may be sensed, compared to other unique signal patterns (based on their respective frequencies) and matched with "similar-frequency" unique signal patterns. Sensing, comparing and matching unique signal patterns may occur over the entire span of a cardiac chamber. For example, multiple locations may include locations throughout the entire left or right atrium or ventricle. Further, matching "similar-frequency" unique signal patterns of high-resolution data from a number of localized regions across a cardiac chamber may produce a high-resolution, global activation map of cellular activity from an entire cardiac chamber.

In can be appreciated that a variety of algorithms, operations, logic rules, processes and/or computations can be utilized to compare frequencies calculated from multiple locations. As stated, one example may include identifying a threshold correlation value that defines whether unique signal patterns should be matched across regions. Further, if no frequencies are found to be with the correlation value, "pairs" of unique signal patterns from a region may be summed and compared to the frequency of other unique signal patterns from other regions. The processing system 32 may implement an iterative process in which matched signal patterns are eliminated from the matching process and remaining frequencies are compared based on the same or a different correlation value.

Figure 4:
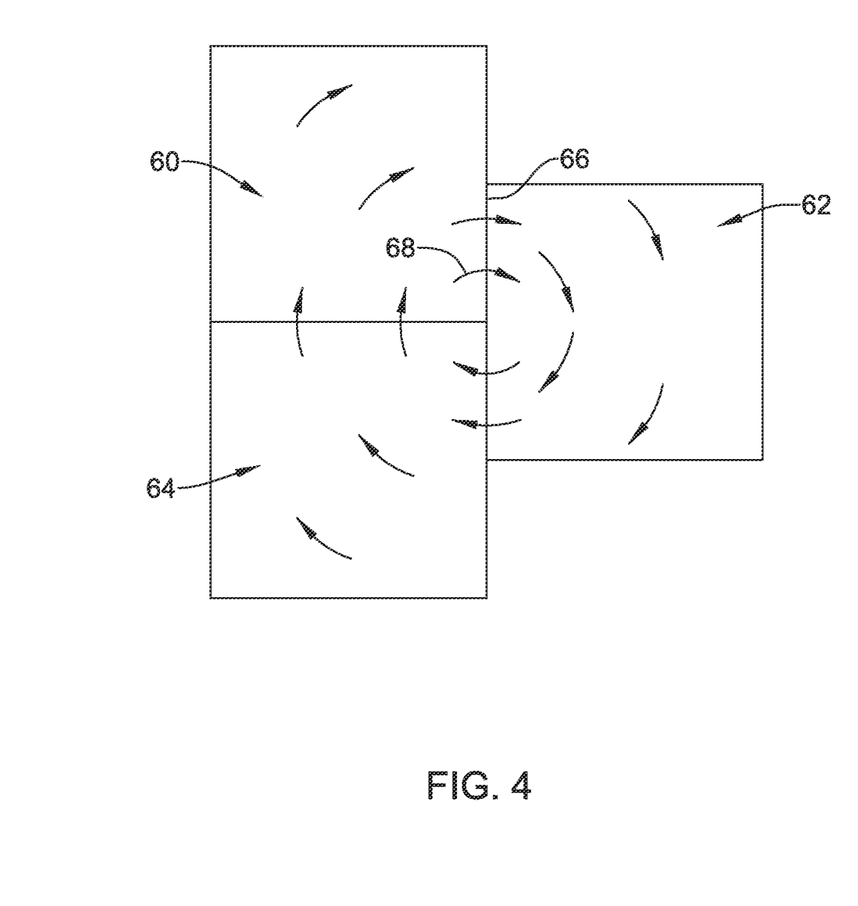
FIG. 4 is a schematic view of an example dominant rotor signal pattern extending across three vector field patterns.

In another embodiment, matching a first signal from a first set of signals with a second signal from the second set of signals to generate a high resolution map of electrical activation data collected from localized regions within a cardiac chamber may include matching by aligning visual representations of the unique signal patterns. For example, FIG. 4 illustrates a schematic dominant rotor signal pattern extending across three example vector field maps 60, 62, 64. It can be appreciated that a variety of visual representations may include, but are not limited to, contour maps, isochrones lines, activation potential displays, and/or phase maps. Unique signal patterns may be aligned based on a particular characteristic inherent to the particular pattern being utilized. For example, FIG. 4 illustrates a schematic visual representation of a vector 68 extending from vector field map 60, across intersection 66, and into vector field map 62. Vector 68 represents the magnitude and direction of an example cellular wavefront propagation sensed by an electrode at a particular location within the heart. FIG. 4 further illustrates that the "visual representation" may be represented by specific pixels or visual components on a display. The pixels and/or visual components may be aligned as the vector extends across intersection 66. Further, FIG. 4 illustrates that a vector field map may include one or more vectors that visually represent a unique signal pattern (e.g. dominant rotor pattern). Therefore, it can be appreciated that the alignment of several visual characteristics may be utilized to accurately align the visual representations of the unique signal pattern. It can also be appreciated that a unique signal pattern may extend over one or more intersections.

In at least some embodiments, unique signal patterns may overlap. One way to align unique signal patterns may be to identify a region of overlap of the signal pattern. The region of overlap may include a region of pixels, a visual indicator, an area of illumination, a display element, an image element or similar visual characteristics that permit a unique signal pattern to be aligned by aligning the overlapped portion of the visual representation (e.g. vector field representation). It is also contemplated that unique signal pattern characteristics (e.g. a vector arrow) may be aligned in a continuous manner (e.g. extending across intersections when positioned adjacent), aligned by overlapping identical elements of the characteristic when positioned in an overlapping configuration, or both in a continuous and overlapping manner.

In another embodiment, unique signal patterns may not overlap. One way to align unique signal patterns that do not overlap may include identifying a region in which the patterns are positioned adjacent to one another. The region in which patterns are adjacent to one another may include a region of pixels, a visual indicator, an area of illumination, a display element, an image element or similar visual characteristics that permit a unique signal pattern to be aligned by aligning the overlapped portion of the visual representation (e.g. vector field representation). Further, aligning the unique signal patterns that do not overlap may include matching an activity gradient. Matching an activity gradient may include a direction of propagation in the region in which the patterns are adjacent to one another (e.g. region of pixels). Determining the activity gradient may include obtaining a direction of propagation. The direction of propagation may be determined using a time-derivative.

Matching a first signal from a first set of signals with a second signal from the second set of signals to generate a high resolution map of electrical activation data collected from localized regions within a cardiac chamber may include comparing unique signal patterns to one or more global template patterns. Example global template patterns may include, but are not limited to, divergent field, curl field or laminar field patterns. Global template patterns may be identified and stored by processing system 32. However, it is contemplated that global signature patterns may be stored, accessed, processed, retrieved and/or utilized in other mediums that may not be connected and/or associated with processing system 32. After a unique signal pattern is sensed by a multiple electrode structure 20, the unique signal pattern may be compared to an example first global template pattern or set of patterns. In at least some embodiments, the global templates may be pre-determined or otherwise known to the clinician. The similarity of the unique signal pattern to the global template pattern may be based on projections of the global template patterns. The unique signal pattern may then be iteratively compared the remaining global template patterns.

Matching a first signal from a first set of signals with a second signal from the second set of signals to generate a high resolution map of electrical activation data collected from localized regions within a cardiac chamber may include any combination of matching according to the frequency at which particular activation patterns in the regions occur over a given time period, matching by unique signal patterns to one or more global template patterns, and/or matching by aligning visual representations of the unique signal patterns. For example, the frequency of unique signal patterns may be calculated after initially matching the unique signal patterns by aligning the visual representations of the patterns. Calculating the frequency after matching by alignment may establish a level of "confidence" of the matching by alignment. Similarly, the frequency of unique signal patterns may be calculated to establish a level of "confidence" for unique signal patterns initially matched by comparing unique signal patterns to one or more global template patterns.

In another embodiment, regional anatomical fingerprints may be generated. Regional fingerprints of localized cardiac regions may be later utilized in reconstruction of an entire cardiac region map. Fingerprinting involves recording the underlying anatomy targeted for mapping. An example step may include generating an impedance map of each region. Another example step may include generating a contour map of each region.

In another embodiment, the period of time to sense and collect data (e.g. sampling duration) may be extended until a unique signal pattern repeats itself. The period of time may also include a maximum threshold.

In another embodiment, global atrial activity may be used to match unique signal patterns. For example, p-wave morphology may be compared across a series of heartbeats to identify activation signals that may be matched to construct cardiac region maps. Further, the timing of p-wave morphology may be used to construct cardiac region maps.

In another embodiment, combining several smaller high-resolution propagation maps may generate a high-resolution cellular wavefront propagation map. FIG. 5 illustrates a schematic cellular activation wavefront propagating in the direction of nine electrodes arranged in a 3×3 electrode distribution 72. The three-dimensional coordinate of each electrode may be sensed using a magnetic and/or impedance-based sensing system. The electrode configuration in FIG. 5 may be representative of nine electrodes arranged on a constellation catheter, basket structure or similar sensing device. FIG. 5 generally illustrates the direction of cellular firing by the wavefront 70, traveling toward the nine electrodes 72. As cells underlying any electrode depolarize in response to a change in electrical membrane potential, an electrode may "sense" an "activation event," i.e. a change in electrical potential relative to the cells' resting state potential. Further, the electrode may collect and send the change in electrical potential data to a processing system 32 which may output the signal to a display 40. Similarly, if adjacent cells fire in response to a change in electrical potential of adjacent cells, the wavefront may propagate to adjacent electrodes. Adjacent electrodes may then sense the change in electrical potential in a similar manner. The time lapse between the sensing of a change in electrical potential of cellular firing between any electrodes can be characterized as a latency time interval between those electrodes. The latency time interval may be used to calculate a direction of the wavefront propagation. Further, as indicated above, the direction of wavefront propagation may be displayed visually as a vector on a vector field pattern, for example.

Figure 5A:
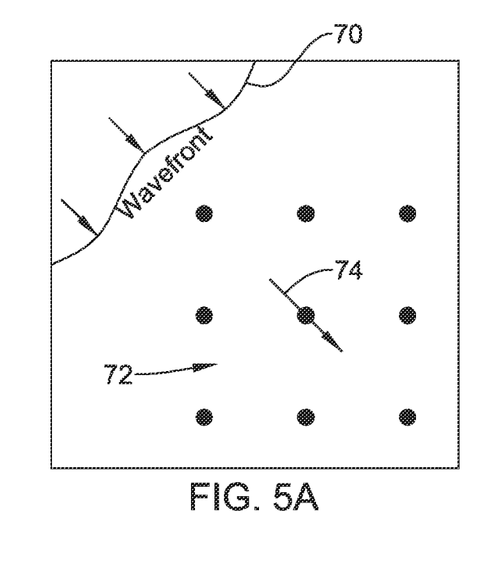
FIGS. 5a-5c are example schematic illustrations of cellular activation vector arrows representing cellular activation wavefront propagation.
Figure 5B:
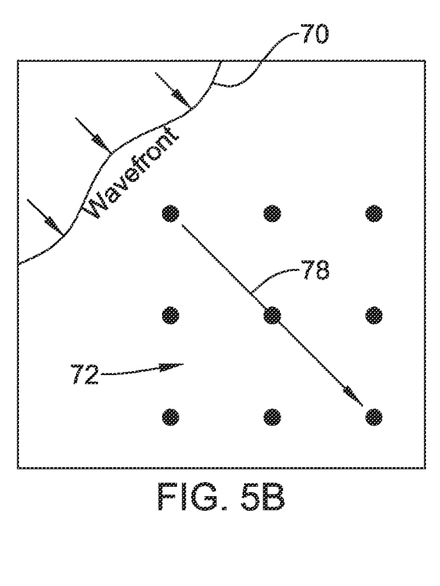
Figure 5C:
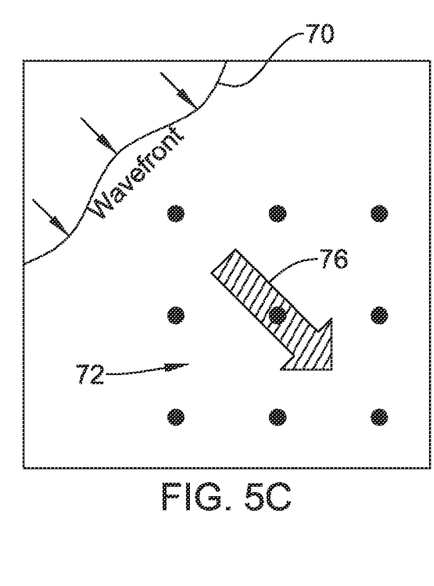

FIG. 5A illustrates a schematic vector 74 located over the center electrode in the nine electrode distribution 72. As indicated above, the magnitude and direction of the vector arrow 74 may be determined by calculating the latency time interval between the center electrode and the surrounding electrodes. Further, the latency time interval may be used to calculate the "dominant" direction of propagation of the activation wavefront 70 across all nine electrodes. The dominant direction electrode may be representative of the general direction of the wavefront propagation as it passes over the collection of the nine electrode distribution 72. In some embodiments, the dominant direction may be represented as an arrow or a display. It is contemplated that any number and configuration of electrode distributions are possible. Further, electrodes utilized to calculate the dominant direction may or may not be adjacent to one another. The vector 74 may represent the dominant direction of propagation of the wavefront 72. As illustrated in FIG. 5A, the arrow that is used to represent the vector 74 has a length and thickness. The length and/or thickness may correlate to the "confidence" with which the processing system 32 has calculated the dominant direction vector. Further, the "confidence" may be directly proportional to the total number of cellular activations occurring in that particular direction over a time period. For example, as illustrated in FIG. 5B, arrow 78 representing the dominant direction on a visual display may be lengthened in response to an increased number of activations sensed in the dominant direction. FIG. 5C illustrates another embodiment in which vector arrow 78 is widened or thickened in response to an increased number of activations sensed in the dominant direction. It is contemplated that any attribute of any visual representation (e.g. vector arrow) may be changed to reflect a level of confidence (e.g. color, shape, transparency). Calculations of dominant direction representations may be generated at many sampling locations within a cardiac chamber. The sampling locations may overlap. Analyzing information from overlapping sampling locations may provide increased confidence levels. The local dominant direction representations may be combined to generate a high-resolution propagation map of the entire cardiac chamber.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

What is claimed is:

1. A medical device, comprising:
    a catheter shaft with a plurality of electrodes coupled thereto, wherein the plurality of electrodes are disposed within a body chamber and are configured to: sense a first set of signals from a first location of the body chamber during a first time period and sense a second set of signals from a second location of the body chamber during a second time period;
    a processor communicatively coupled to the plurality of electrodes, wherein the processor is configured to:
    receive first signals from the catheter corresponding to the first set of sensed signals;
    receive second signals from the catheter corresponding to the second set of sensed signals;
    characterize the first received signals over the first time period;
    characterize the second received signals over the second time period;
    compare the first characterized signals to the second characterized signals; and
    match a first signal from the first characterized signals with a second signal from the second characterized signals.

2. The medical device of claim 1, wherein to sense the first and second sets of signals, the plurality of electrodes are configured to sense a change in electrical potential over the first and second time periods.

3. The medical device of claim 1, wherein the plurality of electrodes are disposed on a basket electrode structure.

4. The medical device of claim 1, wherein to characterize the first received signals, the processor is configured to generate a first unique signal pattern and wherein to characterize the second received signals, the processor is configured to generate a second unique signal pattern.

5. The medical device of claim 4, wherein to characterize the first received signals, the processor is configured to determine a first number of occurrences of the first unique signal pattern during the first time period.

6. The medical device of claim 5, wherein to characterize the first received signals, the processor is configured to calculate a first frequency of the first unique signal pattern during the first time period, wherein the first frequency of the first unique signal pattern is determined by dividing the first number of occurrences of the first unique signal pattern by the first time period.

7. The medical device of claim 6, wherein to characterize the second received signals, the processor is configured to determine a second number of occurrences of the second unique signal pattern during the second time period.

8. The medical device of claim 7, wherein to characterize the second received signals, the processor is configured to calculate a second frequency of the second unique signal pattern during the second time period, wherein the second frequency of the second unique signal pattern is determined by dividing the second number of occurrences of the second unique signal pattern by the second time period.

9. The medical device of claim 8, wherein to match a first signal from the first characterized signals with a second signal from the second characterized signals, the processor is configured to match the first frequency with the second frequency.

10. The medical device of claim 9, wherein the processor is further configured to match additional unique signal patterns and use the matched signal patterns to generate a high resolution map.

11. The medical device of claim 4, wherein to match a first signal from the first characterized signals with a second signal from the second characterized signals, the processor is configured to align the first unique signal pattern with the second unique signal pattern.

12. The medical device of claim 11, wherein to align the first unique signal pattern with the second unique signal pattern, the processor is configured to identify a region of overlap between the first unique signal pattern and the second unique signal pattern.

13. The medical device of claim 12, wherein to align the first unique signal pattern with the second unique signal pattern, the processor is configured to determine and match a first activity gradient of the first unique signal pattern with a second activity gradient of the second unique signal pattern.

14. The medical device of claim 13, wherein the processor is further configured to match additional unique signal patterns and use the matched signal patterns to generate a high resolution map.

15. The medical device of claim 1, wherein the plurality of electrodes are configured to sense one or more additional sets of signals from one or more additional locations during one or more additional time periods.

16. The medical device of claim 4, wherein to match a first signal from the first characterized signals with a second signal from the second characterized signals, the processor is configured to match the first unique signal pattern and the second unique signal pattern to a signal template.

17. A method for mapping electrical activity within the heart, the method comprising:
    providing a catheter having a first electrode and a plurality of additional electrodes adjacent to the first electrode;
    sensing one or more signals over a time period with the first electrode and with the additional electrodes;
    calculating one or more latencies between the first electrode and one or more of the plurality of electrodes over the time period;
    using the one or more latencies to determine one or more directions of the one or more signals between the first electrode and one or more of the plurality of electrodes; and
    determining a dominant direction signal from the one or more directions, wherein the dominant direction signal is representative of a direction of a wavefront propagation.

18. The method of claim 17, further comprising representing, on a display device, the determined dominant direction signal as a vector.

19. The method of claim 18, wherein one or more attributes of the vector are representative of a confidence in the determined dominant direction signal.

20. The method of claim 19, wherein the confidence in the determined dominant direction signal is proportional to a total number of sensed one or more signals occurring in a direction of the vector over the time period.

* * * * *